US009777260B2

(12) United States Patent
Roy et al.

(10) Patent No.: US 9,777,260 B2
(45) Date of Patent: Oct. 3, 2017

(54) VECTORS

(71) Applicant: London School of Hygiene and Tropical Medicine, London (GB)

(72) Inventors: Polly Roy, London (GB); Robert James Noad, Hertfordshire (GB)

(73) Assignee: London School of Hygiene and Tropical Medicine, London (GB)

( * ) Notice: Subject to any disclaimer, the term of this patent is extended or adjusted under 35 U.S.C. 154(b) by 0 days.

(21) Appl. No.: 14/953,513

(22) Filed: Nov. 30, 2015

(65) Prior Publication Data

US 2016/0090575 A1 Mar. 31, 2016

Related U.S. Application Data

(62) Division of application No. 13/128,629, filed as application No. PCT/GB2009/002647 on Nov. 11, 2009, now Pat. No. 9,212,374.

(30) Foreign Application Priority Data

Nov. 11, 2008 (GB) .................................. 0820631.0

(51) Int. Cl.

| | |
|---|---|
| ***C12N 15/00*** | (2006.01) |
| ***C12N 5/00*** | (2006.01) |
| ***C12P 21/06*** | (2006.01) |
| ***C12N 7/00*** | (2006.01) |
| ***C07K 14/005*** | (2006.01) |
| ***C12N 15/86*** | (2006.01) |
| ***C12N 15/63*** | (2006.01) |

(52) U.S. Cl.

CPC .............. *C12N 7/00* (2013.01); *C07K 14/005* (2013.01); *C12N 15/63* (2013.01); *C12N 15/86* (2013.01); *C12N 2710/14021* (2013.01); *C12N 2710/14043* (2013.01); *C12N 2710/14052* (2013.01); *C12N 2710/14121* (2013.01); *C12N 2710/14143* (2013.01); *C12N 2800/30* (2013.01)

(58) Field of Classification Search

None

See application file for complete search history.

(56) References Cited

U.S. PATENT DOCUMENTS

| | | | |
|---|---|---|---|
| 9,212,374 B2 | 12/2015 | Roy et al. |
| 2004/0033596 A1 | 2/2004 | Threadgill et al. |
| 2008/0004228 A1 | 1/2008 | Berger et al. |
| 2011/0281261 A1 | 11/2011 | Roy et al. |

FOREIGN PATENT DOCUMENTS

| | | |
|---|---|---|
| WO | WO 02/00875 A2 | 1/2002 |
| WO | WO 03/074714 A1 | 9/2003 |
| WO | WO 2007/054250 A1 | 5/2007 |
| WO | WO 2007/104979 A1 | 9/2007 |

OTHER PUBLICATIONS

Berger et al., Baculovirus Expression System for Heterologous Multiprotein Complexes, *Nat Biotechnol.* 22:1583-1587, 2004.

Ciccarone, et al., "Generation of Recombinant Baculovirus DNA in *E. coli* Using a Baculovirus Shuttle Vector," *Methods Mol Med.* 13:213-235, 1997.

Definition of "flanking" and "flanked" in Free Online Dictionary by Farlex downloaded Jul. 12, 2013.

Definition of "flanking" and "flanked" in Merriam's Webster Online Dictionary downloaded Jul. 12, 2013.

Fitzgerald et al., "Protein Complex Expression by Using Multigene Baculoviral Vectors," *Nature Methods* 3:1021-1032, 2006.

Noad et al., "Multigene Expression of Protein Complexes by Iterative Modification of Genomic Bacmid DNA," *BMC Mol Biol.* 10:87, 2009.

Yamagishi et al., "The AcMNPV pp31 Gene is not Essential for Productive AcMNPV Replication or Late Gene Transcription but Appears to Increase Levels of Most Viral Transcripts," *Virology* 365:34-47, 2007.

*Primary Examiner* — Catherine S Hibbert

(74) *Attorney, Agent, or Firm* — Klarquist Sparkman, LLP

(57) ABSTRACT

The present invention relates to a transfer vector for inserting a gene into a genetic locus of a baculovirus sequence. The transfer vector comprises an expression cassette comprising a eukaryotic promoter operably linked to the gene and a bipartite selection cassette. The present invention also relates to methods of using the transfer vector and derived bacmids and baculoviruses.

9 Claims, 8 Drawing Sheets

FIG. 3B

| Locus | Insertion | Additional notes |
|---|---|---|
| ctx | 2235 | KO ATG of CTX protein |
| orf11 | 8456 | Insertion into orf |
| egt | 11634-12486 | Deletion in EGT coding seq |
| orf23 | 18755-20243 | Insertion into and partial deletion of orf |
| v-fgf | 27586 | KO ATG of v-FGF |
| 39k | 29226 | Insertion between v-ubiquitin and 39K |
| orf51 | 44285 | Insertion between orf51 and orf52 |
| gp37 | 52275 | Insertion between DNApol and gp37 genes |
| iap2 | 61113-61616 | Deletion in IAP2 coding sequence |
| chiA | 105470-107946 | Deletion of chiA and v-cath genes |
| pe | 110903 | KO ATG of PE protein |
| odv-e18 | 125153 | KO ATG of ODV-E18 |
| odv-e56 | 130010 | Insertion into orf |

FIG. 3A

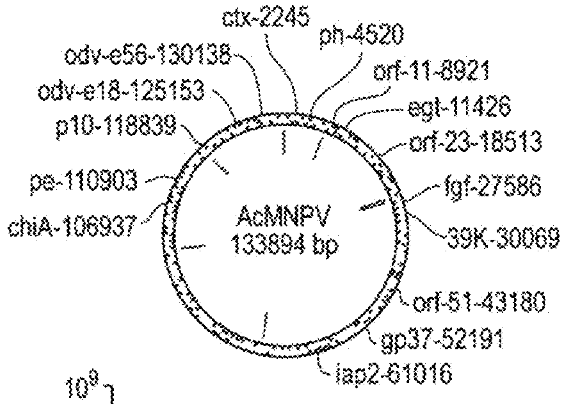

FIG. 3C

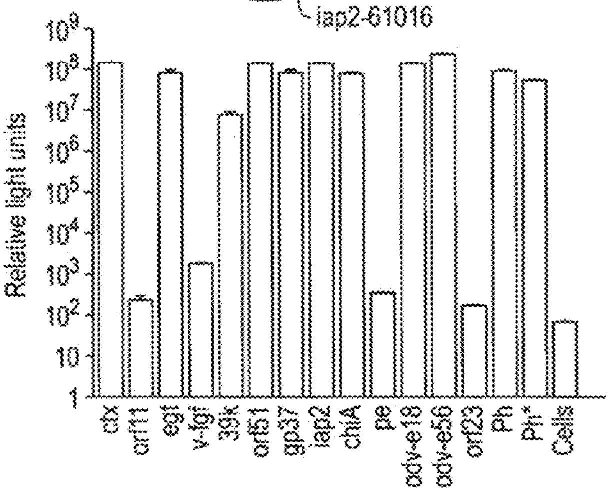

FIG. 3D
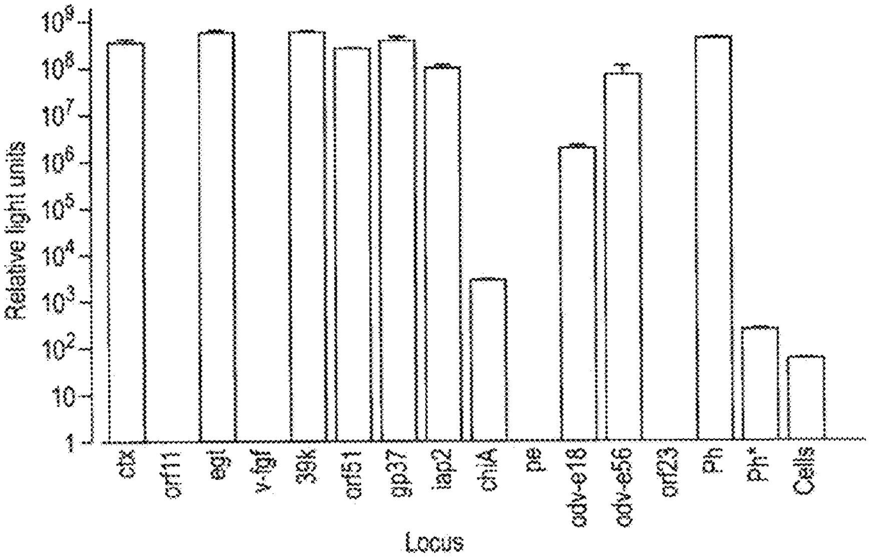
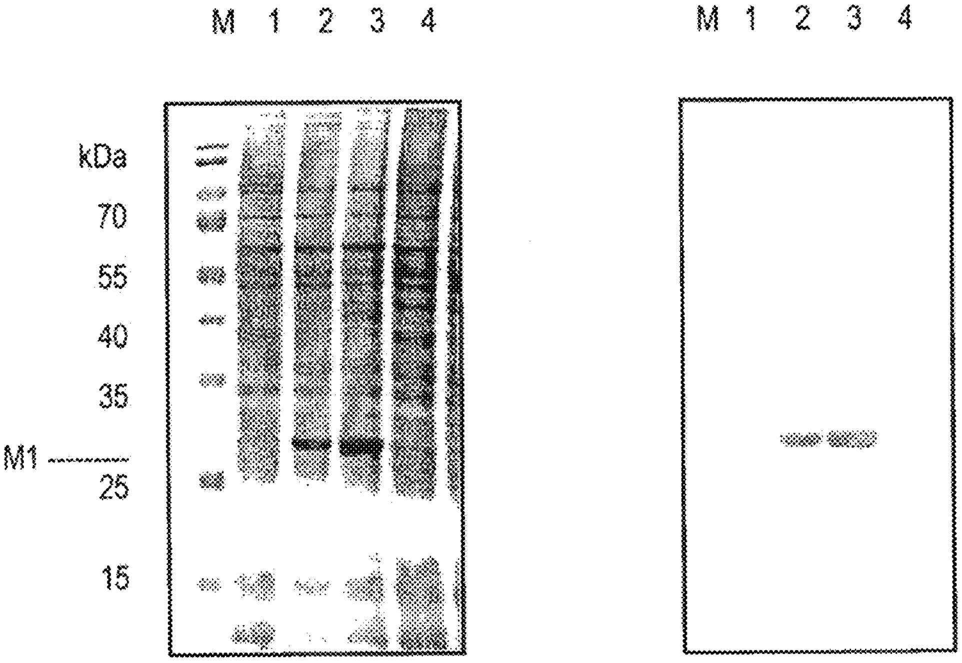
FIG. 4

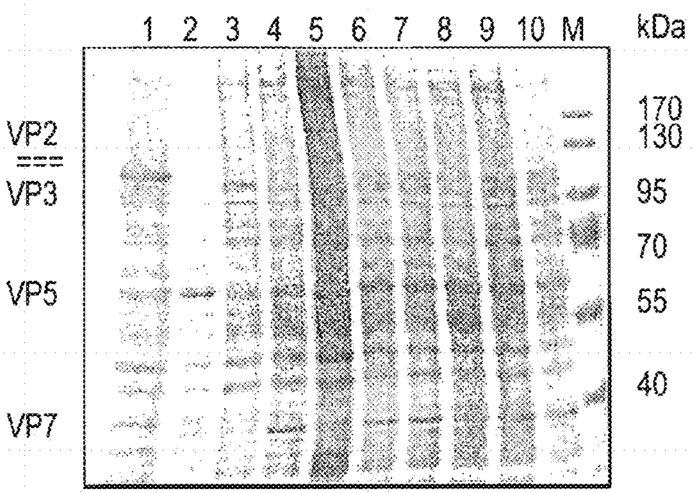
FIG. 6A
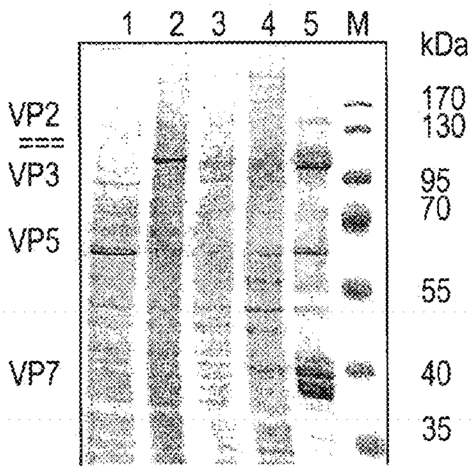
FIG. 6B
| Gene | Locus | Promoter |
|---|---|---|
| BTV1 VP2 | odv-e56 | Ph |
| BTV1 VP5 | p10 | p10 |
| BTV1 VP3 | Polyhedrin | Ph |
| BTV1 VP7 | gp37 | p10 |
FIG. 6C
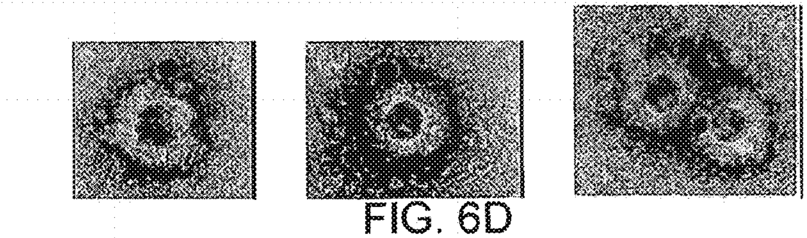
FIG. 6D

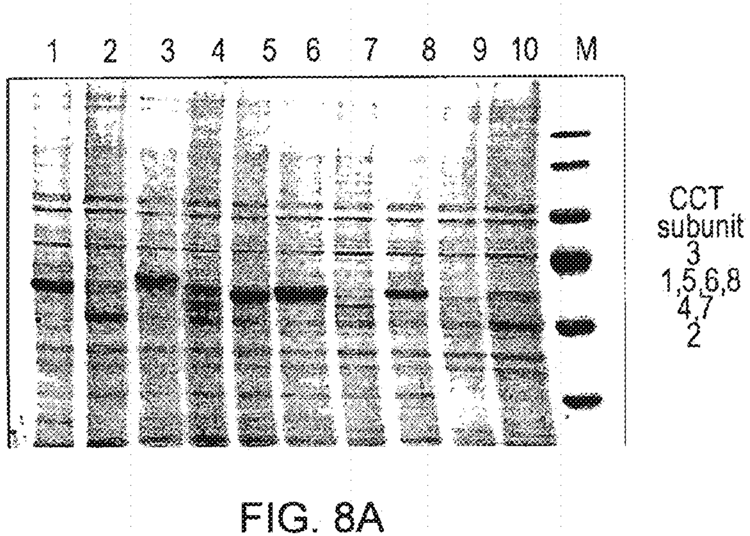
FIG. 8A
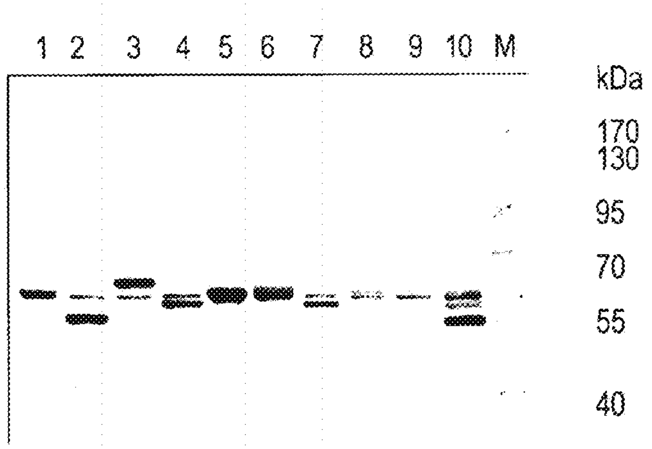
FIG. 8B
| Gene | Locus | Promoter | Gene | Locus | Promoter |
|---|---|---|---|---|---|
| msCCT1 | Polyhedrin | Ph | msCCT5 | gp37 | p10 |
| msCCT2 | p10 | p10 | msCCT6 | odv-e56 | ph |
| msCCT3 | egt | Ph | msCCT7 | ctx | p10 |
| msCCT4 | 39k | p10 | msCCT8 | orf51 | p10 |
FIG. 8C

VECTORS

CROSS REFERENCE TO RELATED APPLICATIONS

This application is a divisional of U.S. Ser. No. 13/128,629 filed Jul. 21, 2011, U.S. Pat. No. 9,212,374, which is the U.S. National Stage of PCT/GB2009/002647 filed Nov. 11, 2009, which claims priority to GB 0820631.1 filed Nov. 11, 2008.

FIELD

The present invention relates to a transfer vector for inserting a gene into a genetic locus of a baculovirus sequence. The present invention also relates to methods of using the transfer vector and derived bacmids and baculoviruses.

BACKGROUND

The baculovirus expression system has been used to express many thousands of proteins in eukaryotic cells for structural and biochemical studies (14). In addition to its ability to express single recombinant proteins the baculovirus system has also been used to co-express multiple proteins that form complexes (15-22). This is important as genome-wide interaction screens are revealing that many critical functions of living cells are carried out by multi-subunit protein complexes (23). Two main strategies have been used to achieve co-expression of proteins using the baculovirus system. The coinfection of cells with two or more viruses each of which expresses one recombinant protein is by far the most common approach (19,24,25). However, often yields of protein complexes from these studies are very variable and co-infection of the same cells by two different baculoviruses does not follow the poisson distribution (26). Thus while the co-infection approach is technically straightforward, it is practically limited to recovery of relatively simple complexes for applications that do not require large amounts of purified proteins.

For applications such as structural studies and large vaccine trials where more protein is required, and for more complicated complexes formed from many subunits, the alternative approach of co-expressing proteins from multiple similar expression cassettes inserted at the polyhedrin or P10 loci has been used (15-18,22,27). This approach has the advantage that every cell in the culture that is infected with recombinant virus expresses all of the proteins required for formation of the protein complex in a reproducible manner. Where the coinfection and single baculovirus approaches have been compared, the latter has demonstrated significantly better yield of recombinant complex (28). However, expression of multiple proteins using a single recombinant virus is not without drawbacks. Although rod shaped baculovirus appears quite tolerant of insertions in its genome, genes are transferred to the virus by homologous recombination and the transfer vector must be of a size that is easily manipulated in *E. coli*. Therefore there is a limit to the number of genes that can be inserted into a transfer vector. In practice this means that it is rarely possible to express more than four proteins from a single locus. In addition, baculoviruses contain sequences and express proteins that promote homologous recombination (29-32). Therefore viruses that contain large amounts of repeated sequence are prone to rearrangement and recombination (21,33,34).

The single baculovirus coexpression approach has been modified by insertion of a loxP site at the chiA/cathepsin locus of a bacmid that already contains the Tn7 target at the polyhedrin locus (20). This allows insertion of multiple expression cassettes at each of these loci using recombination in *E. coli*. As might be expected given that this system relies on the iterative duplication of an expression cassette that has been modified to express different genes there is evidence that inserts into this system are somewhat unstable genetically (21).

Recently baculovirus research has benefited from use of the ET recombination system which has allowed selective knockout of viral genes (35-49). However, the potential for this technique to engineer and facilitate the expression of proteins at genetic loci other than p10 and polyhedrin has not been examined.

The present invention relates to a method for the efficient expression of multiple recombinant proteins (i.e., non-baculoviral proteins) from a single baculovirus genome. The method allows single protein expression cassettes to be inserted efficiently at different loci within the viral genome using the ET recombination system. Furthermore, the method allows for the expression of complexes with numerous subunits.

The expression of single proteins using baculovirus as an expression system is well established. The basic methodology of the expression system has changed very little since its first production. At 133 kb the baculovirus dsDNA genome is too large to manipulate directly. Genes encoding foreign proteins are therefore cloned, in *E. coli*, into vectors containing an expression cassette from the AcMNPV insect virus and this is then introduced with viral DNA into insect cells where viral and cellular proteins mediate homologous recombination that results in the production of an infectious (with respect to insect cells) virus that expresses the foreign protein. Some variations on this theme have already been generated, including viral genomes that only replicate if recombination occurs (1,2), and performing recombination in *E. coli* with a bacmid based on the use of transposon Tn7 (3) to speed up the selection of recombinant virus. The expression of multi-protein complexes in insect cells has also been achieved using the baculovirus expression system as briefly discussed above. Initially, multiple viruses each expressing a single protein were used to co-infect susceptible cells and the protein complex purified after expression. However, this is at best inefficient and not reproducible enough to be feasible for scale-up. As an alternative, vectors that incorporate multiple expression units but recombine with a single virus genetic locus were produced (4-6). These vectors had the advantage that they produced all recombinant protein subunits in the every infected cell and resulted in significantly higher yields of recombinant protein complex. In addition, because only a single virus expresses all the proteins the results of infections were much more reproducible. The disadvantage of these vectors is twofold. Firstly, because the vectors contain repeated sequences and the baculovirus expresses proteins that promote homologous recombination, expression, particularly from constructs containing three or four expression units, is not always very stable genetically through large numbers of viral passages (which are necessary during industrial scale-up for baculovirus protein expression). Secondly, there is a practical limit to the size of insert that can be easily maintained and manipulated in *E. coli* which limits the number of proteins that can be expressed from these vectors. Another approach that has been proposed for the production of multiple proteins is the insertion of foreign protein(s) at one genetic locus in baculovirus, then selection of virus expressing that protein and the use of this viral genome to recombine at a second genetic locus to express other proteins (7). However, because of the high degree of technical skill and amount of time involved in this approach (16 days for the first locus and 25 days for each subsequent locus) this approach has hardly ever been used. A recent development was to modify the BAC based Tn7 transposon system to insert a LoxP site at a second genetic locus in baculovirus to also allow the insertion of extra genes at this locus in *E. coli* (8). However, this method still suffers from the problems that repeat sequences from duplication of promoters in the bacterial vectors will mean that the construct is genetically unstable for multiple viral passages and transfer vectors will quickly reach the maximum practical size for manipulation in *E. coli*.

The method of the present invention overcomes at least some of the problems inherent in the prior methods, such as genetic instability and the requirement for multiple rounds of recombination.

SUMMARY

According to a first aspect, the present invention provides a transfer vector for inserting a gene into a genetic locus of a baculovirus sequence comprising:

an expression cassette comprising a eukaryotic promoter operably linked to the gene;

a bipartite selection cassette comprising:

(i) an expressible sequence encoding a first selectable marker; and (ii) an expressible sequence encoding a second selectable marker; and sequences flanking the expression and bipartite selection cassettes, wherein the sequences substantially correspond to sequences of the genetic locus within the baculovirus sequence.

The transfer vector of the present invention can be used to efficiently insert a gene into a genetic locus of a baculovirus sequence and to select for the baculovirus sequences that comprise the gene. In particular, it has been found that by using a bipartite selection cassette a substantial increase in identification of positive clones (i.e., baculovirus sequences containing the inserted gene) was obtained compared to selection using a single selection marker. This provides a significant advantage over the use of a single selection marker. Only a small number of baculoviruses are transformed and hence the marker is only expressed at very low levels. For example, when the marker is antibiotic resistant only very low levels of antibiotic can be used. This results in the selection of bacterial variants that are resistant to the antibiotic used. Hence some bacteria growing on the plates may not contain the modification. Using two positive selection methods overcomes the possibility of such false positive selections.

The transfer vector of the present invention can be any suitable vector, provided it is capable of recombining with a baculovirus sequence via homologous recombination to insert a gene into the baculovirus sequence. Suitable transfer vectors are well known to those skilled in the art. Key features of the transfer vector are discussed further below.

The gene to be inserted into the baculovirus sequence can be any heterologous gene (i.e., non-baculoviral gene). It is preferred that the heterologous gene encodes a subunit of a protein complex. The heterologous gene may encode a viral protein, a component of a receptor or a chaperone complex. It is particularly preferred that the heterologous gene encodes a viral protein that together with other viral proteins can form a virus like particle (VLP).

The genetic locus at which the gene is inserted into the baculovirus sequence can be any suitable locus that allows expression of the inserted gene and also does not prevent the ability of the baculovirus sequence from replicating. Further, the locus used should not affect the ability of baculovirus to infect cells, i.e. replicate or spread from cell to cell. Such loci include the polyhedrin and the p10 loci. Further additional suitable loci identified by the present inventors include ctx, egt, 39k, orf51, gp37, iap2 and odv-e56.

The baculovirus sequence can be any suitable baculovirus sequence that can replicate in an insect cell and a prokaryotic cell such as *E. coli*. In particular, any viral baculovirus genome that contains a BAC replicon may be used. Suitable baculovirus sequences include the AcMNPV bacmid.

The term "expression cassette" refers to the combination of elements required for expression of the gene. Accordingly, the expression cassette comprises a suitable promoter allowing expression of the encoded gene in eukaryotic cells (i.e., insect cells), and a suitable polyadenylation signal sequence flanking the gene sequence. Expression cassettes for the expression of genes in eukaryotic cells are well known to those skilled in the art. Particularly preferred promoters include the baculovirus viral late promoters (e.g. p35) or viral very late promoters (e.g. polyhedrin and p10 promoters). Suitable polyadenylation signal sequences include the tryptophan hydroxylase (Tph) polyadenylation sequence, or polyadenylation sequences from baculovirus genes.

The expression cassette can comprise more than one gene (e.g., 2, 3 or 4 genes) resulting in the expression of more than one gene. However, generally, it is preferred that the expression cassette comprises a single gene.

The bipartite selection cassette has been found to improve the identification and isolation of clones that have successfully received the gene. The bipartite selection cassette comprises 2 different selectable markers. The cassette also comprises any elements required for expression of the markers in a bacterial cell such as one or more bacterial promoters. The step of selecting sequences that have received the gene comprises selecting for sequences that comprise both the selectable markers. This selection step is carried out in bacterial cells, e.g., *E. coli*. The selectable markers may be any markers that allow the cells comprising the cassette to be selected. For example, the markers may be visible such as a marker that causes the appearance or change of colour of a cell or colony. Alternatively, the marker may confer resistance to, for example, an antibiotic. The two selectable markers may be the same type of marker, e.g. resistance to two different antibiotics, or different types of marker, e.g. antibiotic resistance and a visual marker. The first selectable marker is preferably a visual marker, such as the LacZalpha fragment, which allows cells expressing the LacZalpha fragment to appear blue in the presence of IPTG and X-gal. The second selectable marker is preferably any marker that confers antibiotic resistance, such as resistance to chloramphenicol, tetracycline, puromycin, ampicillin, penicillin, apramycin, kanamycin or phleomycin. It is particularly preferred that the second marker confers resistance to phleomycin.

In a preferred embodiment the bipartite selection cassette is flanked by LoxP recombination sequences. LoxP recombination sequences combine together in the presence of Cre recombinase resulting in the deletion of the intervening sequence. Accordingly, the bipartite selection cassette can be removed enabling the same selectable markers to be used when inserting any additional genes into the baculovirus sequence. Preferably the LoxP sites are modified to ensure that only a single round of recombination can occur between the sites. Suitable modified LoxP sites are known to those skilled in the art, for example, the Lox66 and Lox71 modified sites.

The sequences flanking the expression and bipartite selection cassettes substantially corresponds with sequences of the genetic locus allowing homologous recombination to occur between the transfer vector and the baculovirus sequence. Each flanking sequence is preferably at least 20 bp in length, more preferably at least 30 bp in length and even more preferably at least 50 bp in length, and has a sequence allowing specific recombination with a sequence of the genetic locus.

According to a second aspect, the present invention provides a method for producing a recombinant bacmid comprising:

bringing a bacmid and the transfer vector according to the first aspect of the present invention together to allow homologous recombination; and selecting for a recombinant bacmid that comprises the bipartite selection cassette.

The recombinant bacmid can be selected using standard techniques depending on the bipartite selection cassette.

The method for producing a recombinant bacmid may additionally comprise detecting the presence of the gene in the bacmid or its expression product. Suitable screening techniques can be used depending on the specific gene.

Furthermore, when the selection cassette is flanked by LoxP recombination sequences, the method preferably further comprises inducing recombination between the LoxP sites, e.g., by exposing the bacmid to Cre recombinase, to remove the bipartite selection cassette. The Cre recombinase is preferably under the control of an inducible promoter, such as the arabinose promoter. The advantage of removing the bipartite selection cassette is that a further transfer vector can be recombined with the bacmid, wherein the further transfer vector contains the same bipartite selection cassette. Selection for the further recombined bacmid can be performed using the same techniques as used following the first round of recombination.

Generally, the method of producing a recombinant bacmid is performed in a prokaryotic cell as a prokaryotic cell based system is easier and quicker to manipulate. It is preferred that the prokaryotic cell based system is conducive to homologous recombination. Such systems include the lambda red recombination system, which is described in European patent application EP-A-1291420. Preferably, the method of producing the recombinant bacmid is performed in *E. coli*. It is particularly preferred that the method is performed using *E. coli* cell line EL350, which has both an integrated lambda prophage expressing exo, bet and gam under control of the temperature regulated lambdaPL promoter, and Cre recombinase under control of an arabinose inducible promoter.

The method of producing the recombinant bacmid can be repeated a number of times so that the bacmid can contain a number of heterologous genes, i.e., 1, 2, 3, 4, 5, 6, 7, 8 or more heterologous genes. By endeavoring to use different promoters for expressing each inserted gene and as each gene is inserted at a different genetic locus, it is possible to reduce or avoid having repeated sequences in the bacmid and thereby ensure that the bacmid has good genetic stability. It is further preferred that at least one essential gene is positioned between each inserted heterologous gene. Such an arrangement ensures that if homologous recombination occurs between any of the inserted sequences, an essential gene will be deleted resulting in a non-viable bacmid.

According to a third aspect, the present invention provides a recombinant bacmid obtained by the method according to the second aspect of the present invention. The bacmid comprises the inserted gene and may also comprise remnants of the LoxP sequences. These remnants may be used as markers to identify the bacmids. The bacmid preferably comprises at least 6, 7, 8 or 9 heterologous genes.

According to a fourth aspect, the present invention also provides a method for producing a recombinant baculovirus comprising culturing a eukaryotic cell containing the recombinant bacmid obtained by the method according to the second aspect of the present invention under conditions so that a baculovirus is produced.

Preferably the eukaryotic cells are insect cell, more preferably derived from the insects *Spodoptera frugiperda* or *Trichoplusia ni* e.g. (Sf21, SP or TN 5B-1-4) insect cells. The baculovirus can be isolated using standard techniques and the expression of the inserted heterologous gene tested.

According to a fifth aspect, the present invention also provides a recombinant baculovirus obtained by the method according to the fourth aspect of the present invention.

According to a sixth aspect, the present invention also provides a recombinant bacmid or a recombinant baculovirus that expresses a plurality of heterolgous proteins, wherein each protein is expressed from a separate genetic locus of the bacmid or baculovirus. It is further preferred that at least one essential gene is positioned between each genetic locus expressing a heterologous protein. Such an arrangement ensures that if homologous recombination occurs between genetic loci expressing a heterologous gene an essential gene is deleted resulting in a non-viable bacmid or baculovirus. Preferably the bacmid or baculovirus expresses at least 3, more preferably at least 5 and most preferably at least 8 proteins. The proteins are heterolgous, i.e., are not encoded by naturally occurring baculoviruses. It is further preferred that the encoded heterologous proteins are subunits of a protein complex, such as a VLP, a receptor complex or a chaperone complex.

It is further preferred that the separate genetic loci of the recombinant bacmid or baculovirus are selected from ctx, egt, 39k, orf51, gp37, iap2, odv-e56 and p10. The position of such loci are specifically described with reference to baculovirus AcMNPV in Table 1 below. One skilled in the art can easily determine the location of the loci in other baculovirus strains and bacmids using this information.

TABLE 1

The genetic loci referred to above are defined below with reference to the reference accession sequence for AcMNPV (accession number NC001623).

| Locus | boundaries |
|---|---|
| ctx | 2028-2296 |
| egt | 11310-13091 |
| 39k | 29196-30070 |
| orf51 | 43154-44337 |
| gp37 | 52192-52327 |
| iap2 | 60983-61823 |
| p35 | 116282-117460 |
| p10 | 118767-119135 |
| odv-e56 | 128947-130166 |

According to a seventh aspect, the present invention also provides a recombinant bacmid or a recombinant baculovirus wherein an expression cassette encoding a heterologous protein is inserted at one or more of the following genetic loci: ctx, egt, 39k, orf51, gp37, iap2 and odv-e56.

It has been found that these genetic loci specifically allow high level expression of the heterologous protein without disrupting the essential functions of the bacmid or baculovirus.

Preferably the recombinant bacmid or recombinant baculovirus encodes a plurality of proteins, each expression cassette being inserted at a different genetic locus. It is further preferred that the recombinant bacmid or recombinant baculovirus encodes at least 3, more preferably at least 5 and most preferably at least 8 proteins. It is further preferred that the encoded heterologous proteins are subunits of a protein complex, such as a VLP, a receptor complex or a chaperone complex.

According to an eighth aspect, the present invention also provides a transfer vector for inserting a gene into a genetic locus of a baculovirus sequence comprising:

an expression cassette comprising a eukaryotic promoter operably linked to the gene; and sequences flanking the expression cassette, wherein the sequences substantially correspond to sequences of the genetic locus within the baculovirus sequence, wherein the genetic locus is selected from: ctx, egt, 39k, orf51, gp37, iap2 and odv-e56.

As indicated above, it has been found that by inserting the gene into the recited genetic loci high level expression of the gene can be obtained without disrupting the essential functions of the baculovirus sequence.

According to a ninth aspect, the present invention also provides a method for producing a recombinant bacmid comprising:

bringing a bacmid and the transfer vector according to the eighth aspect of the present invention together to allow homologous recombination; and selecting for a recombinant bacmid that comprises the expression cassette.

Methods for producing such a recombinant bacmid and selecting for such a bacmid are well known to those skilled in the art. The present invention also provides a recombinant bacmid obtained by this method.

According to a tenth aspect, the present invention also provides a method for producing a recombinant baculovirus comprising producing a recombinant bacmid by the method of the present invention and culturing a eukaryotic cell containing the bacmid so that a baculovirus is produced.

Methods for producing such a recombinant baculovirus are well known to those skilled in the art. The present invention also provides a recombinant baculovirus obtained by this method.

The present invention also provides a cell containing a transfer vector, a bacmid, or a baculovirus according to any aspect of the present invention.

The present invention also provides a method for producing one or more proteins comprising culturing the recombinant bacmid or baculovirus according to any aspect of the present invention under suitable conditions. The one or more proteins are encoded by the one or more genes and may combine to form a protein complex such as a VLP or a chaperone complex. The one or more proteins can be isolated using standard techniques well known to those skilled in the art.

BRIEF SUMMARY OF THE DRAWINGS

The present invention is now described by way of example only with reference to the following figures.

FIG. 3A shows identification of additional sites for expression of recombinant proteins in the AcMNPV genome. Cartoon of AcMNPV showing relative positions of loci used for protein expression.

FIG. 3B is atable showing loci used for insertion and any additional changes made to locus.

FIG. 3C is a bar graph showing relative *Renilla* luciferase activity at 48 hours post infection with virus modified to contain an additional firefly luciferase expression cassette at each locus indicated. All viruses had the same *Renilla* luciferase expression cassette at the p10 locus under control of the p35 promoter. Error bars indicted the standard deviation of five replicates for each locus.

FIG. 3D is a bar graph of normalised firefly luciferase activity showing relative expression of a polyhedrin promoter-firefly luciferase polyhedrin terminator cassette inserted at each locus as indicated. Error bars indicate the standard deviation from 5 replicates for each locus. Firefly luciferase was normalised using the *Renilla* luciferase control expressed from the same genome. Firefly luciferase insertions at the orf11, v-fgf, pe and orf23 loci were excluded due to *Renilla* luciferase levels more than 2 logs lower than control virus. Virus Ph has firefly luciferase at the polyhedrin locus and *Renilla* luciferase at the p10 locus. Virus Ph* has the same p10 *Renilla* luciferase insertion but no firefly luciferase insertion.

FIG. 4 shows expression of influenza M1 from egt and polyhedrin loci. Left panel shows Coomassie stained SDS PAGE gel of total protein from cells infected with control baculoviruses (lanes 1 and 4), egt-M1 (lane 2) and YM1-M1 (lane 3). The sizes of protein markers (lane M) are indicated on the left hand side of the gel. Right panel shows Western blot of duplicate gel probed with anti-H7N7 antiserum.

FIG. 6A shows production of baculovirus co-expressing 4 proteins. Cell lysate from cells infected with baculovirus expressing VP2 (lane 1), VP5 (lane 2), VP3 (lane 3) and VP7 (lane 4), uninfected cells (lane 5) or all 4 proteins (lanes 6-10), position of marker proteins (M) and size in kDa is as indicated.

FIG. 6B shows production of baculovirus co-expressing 4 proteins. Cell lysate for cells expressing VP5, VP2, VP3, VP7 (lanes 1-4 and partially purified VLPs (lane 5).

FIG. 6C is a table showing locus of insertion and viral promoter used for expression of each BTV protein.

FIG. 6D shows immunogold negative stain EM (for VP5) showing purified BTV VLPs.

FIG. 8A shows expression of CCT in insect cells. Coomassie stained cell lysate from cells infected with baculovirus expressing CCT1-CCT8 (lanes 1-8, respectively), cells only (lane 9) or baculovirus coexpressing 7 CCT subunits (lane 10).

FIG. 8B shows a Western blot of duplicate gel using polyclonal anti-mouse CCT antiserum.

FIG. 8C includes tables showing different genetic loci and promoters used to express each of the CCT subunits.

EXAMPLES

Figure 1A:
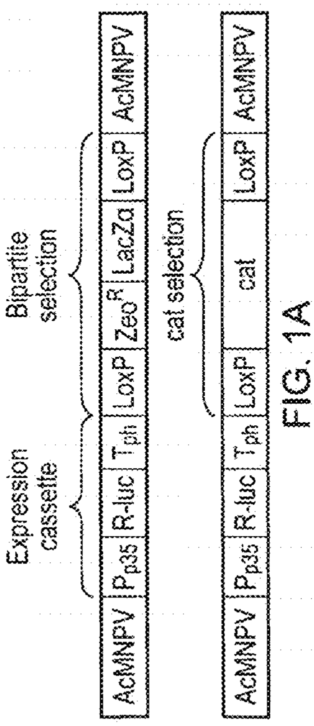
FIG. 1A shows an improved selection of recombinants from ET cloning. Cartoon of DNA used for cat and bipartite recombinations. Both constructs had the same baculovirus flanking sequences (AcMNPV), *Renilla* luciferase expression cassette (Pp35-Rluc-Tph) and loxP sites (LoxP). The bipartite selectable marker also had zeocin resistance gene (ZeoR) and LacZα fragment. In the chloramphenicol resistant construct this was replaced with the cat gene.

The baculovirus expression system has well established potential for the production of large amounts of correctly folded eukaryotic proteins for enzymatic and structural studies. However, it is becoming increasingly clear that many, if not most, proteins are active within cells as complexes made up of the products of several distinct genes. Given the acceleration in the pace of discovery of protein structures, there is a real need to establish systems for the rapid and reliable production and purification of protein complexes. This is particularly true of larger complexes that require the simultaneous expression, and eukaryotic folding and processing, of many protein subunits. Previously the inventors have developed baculovirus transfer vectors capable of expressing 2, 3, 4 and 5 proteins from the same baculovirus genome. The inventors' main goal in the previous studies was to produce a system capable of synthesizing large amounts of viral protein complexes containing non-equimolar amounts of virus encoded proteins for structural and enzymatic studies. One of the observations from experience with these systems is that single baculoviruses expressing multiple genes are much more efficient at forming the desired protein complexes than co-infection of insect cells with multiple baculoviruses expressing single genes. In the current study the inventors have used new technologies to exploit this observation for the production of recombinant baculoviruses expressing multiple proteins for biologically relevant mammalian protein complexes.

In particular, the inventors have adapted and improved new bacterial chromosome engineering technologies for the rapid and efficient production of recombinant baculoviruses expressing multiple proteins simultaneously. The new systems developed are 30 times more efficient than conventional processes and allow the routine insertion of genes at any locus within the baculovirus genome. These studies have allowed identification of 7 new genetic loci within the baculovirus genome that allow high level expression of recombinant protein. Furthermore, the inventors have demonstrated that multiple iterative rounds of recombination can be carried out allowing the generation of virus genomes expressing multiple proteins in a complex from separate single gene insertions. As examples, the inventors have expressed VLP protein complexes for influenza A (H7 subtype) and bluetongue virus (serotype 1), as well as the 8 subunit mammalian chaperone complex CCT (TCP), that is a focus for cancer studies.

Materials & Methods

Multi-locus single gene insertions are achieved in *E. coli* using lambda red recombination. The invention includes the use of baculovirus loci that have not previously been used for multi-protein expression, and the incorporation of selectable markers that can be removed from the baculovirus genome and subsequently reused. Unlike other systems, the recombinant protein genes are not flanked by repeat sequences, improving their genetic stability.

The transfer vectors contain a region of AcMNPV to target homologous recombination, an expression cassette (AcMNPV promoter, polylinker, polyadenylation signal) and a bacterial selection cassette. The AcMNPV promoter used is from either viral late (e.g. p35) or very late (e.g. Polyhedrin, p10) genes. The bacterial selection cassette consists of mutant LoxP site—bacterial selectable marker—mutant Lox P site. The mutant Lox P sites are variants on the LoxP66 and LoxP71 variants (9). The LoxP sites for each selectable marker are designed such that on recombination the marker is deleted destroying the LoxP site that remains. Each selectable marker has different LoxP mutant arms so that recombination between different selectable marker genes inserted in the same baculovirus will not occur.

Choice of System used for Multi-Locus Expression of Recombinant Proteins

The original research plan involved the use of homologous recombination in insect cells, or the alternative method of ET recombination in *E. coli*, to allow efficient insertion of expression cassettes for recombinant proteins at different loci within the baculovirus genome. Our preliminary data had suggested that linearization of transfer vector resulted in a significant increase in the recombination frequency (up to ~30%) at a locus (p10) that did not have positive selection other than the recombinant protein produced. At the start of the research project the two systems (ET recombination and insect cell recombination) were considered with regards to their reproducibility and time taken to complete insertion of a recombinant gene in a particular locus and check expression of the resulting protein. In terms of time taken for each round of expression the ET recombination system was faster, mainly because of reduced time needed to prepare the baculovirus genome for the insertion of genes at a second genetic locus in the baculovirus. In addition it was possible to design an approach that allowed confirmation of genetic insertions independently of transgene expression, and therefore the need to grow virus in insect cells to check expression was less critical than for the wholly insect cell based system. Secondly, although it is possible to co-introduce a marker with inserted genes in the baculovirus system, the number of such markers is limited and each could only be used once. Since one of the goals of the project was to express the mouse CCT (TCP1) complex (8 subunits) the ET recombination approach was adopted as the research priority at an early stage as this system was faster and more able to accommodate multiple genetic insertions.

Example 1

Development of Reagents Allowing Efficient Selection of ET Recombinants

Figure 1B:
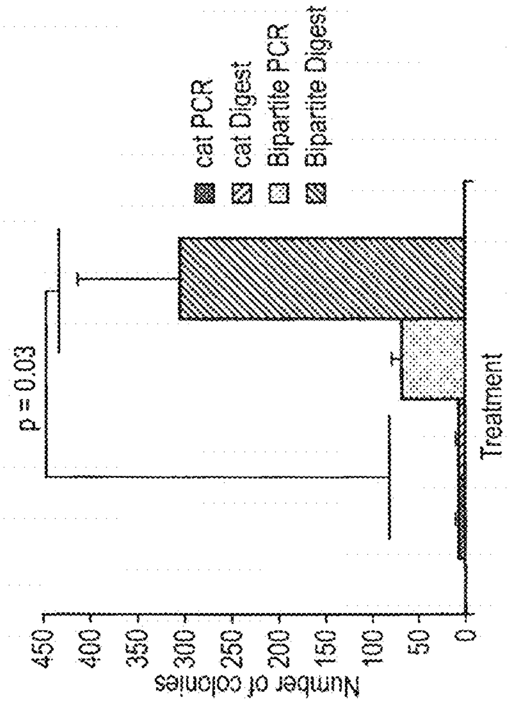
FIG. 1B is a bar graph showing the number of positive bacterial colonies following ET recombination. DNA used for recombination was produced either by PCR or restriction enzyme digest, as indicated.

Initial experiments using the ET approach were disappointing. Experiments were performed in which a reporter gene (luciferase) was inserted into a bacterial artificial chromosome carrying the full AcMNPV genome (Bacmid) and selected for by a chloramphenicol resistance gene that was co-integrated with the luciferase reporter. Although chloramphenicol resistant bacterial colonies were recovered, subsequent analysis revealed that they did not contain the correctly modified Bacmid with the luciferase reporter. Similar results were obtained when the reporter, which was designed to only be expressed in insect cells in the presence of replicating AcMNPV, was changed to GFP. However, when the GFP construct was used for recombination in *E. coli*, without chloramphenicol selection, and Bacmid DNA prepared for the whole transformed *E. coli* population, then this DNA resulted in a few fluorescent foci when transfected into insect cells (Sf21). These data suggested that the problem was not with the recombination itself, but with the post-recombination selection of bacteria containing the insertion. To overcome these problems the inventors designed a new selection cassette that incorporated a bipartite marker system based on LacZα fragment and Zeocin resistance gene flanked by modified LoxP recombination sites (FIG. 1A). Using this system enough Zeocin was added to the selection plates to reduce but not eliminate background colony growth and recombinants were selected based on blue colony phenotype in the presence of IPTG and X-gal. To assess the relative efficiency of recovering recombinants using the chloramphenicol (cat) and bipartite selection systems the inventors carried out an experiment where recombination competent *E. coli* containing unmodified Bacmid were electroporated with 30 ng (~12.5 fmol) of either the chloramphenicol based or bipartite selection cassette (FIG. 1B). As an ideal system for incorporation of foreign protein coding sequences would not involve repeated PCR of the inserted gene the inventors also compared the efficiency of recombination between the PCR amplified DNA, that is the routine for ET recombination, and restriction enzyme released, gel purified, DNA. PCR primers were designed such that the ends of the PCR products corresponded to the ends of the restriction enzyme released fragments.

Figure 1C:
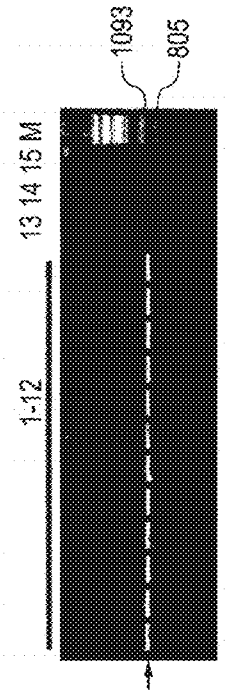
FIG. 1C is a digital image showing the correct insertion of Rluc expression cassette confirmed by PCR using one primer in the transferred DNA and one flanking the target locus in the baculovirus DNA. The correct PCR product (arrowed) would only be produced following correct integration. Results for 12 independent recombinants (1-12), no template PCR control (13), unmodified bacmid template (14) and transfer DNA template (15) are shown. Lane M is marker DNA.
Figure 1D:
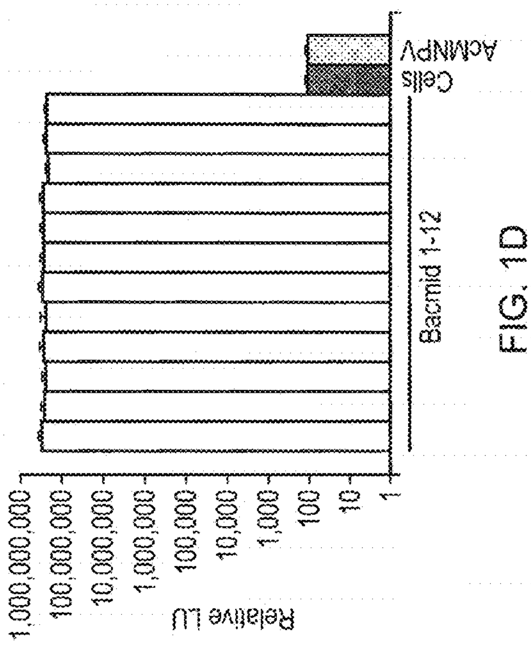
FIG. 1D is a bar graph showing *renilla* luciferase activity (relative light units) at 48 hours post infection in cell lysate from cells infected with passage 2 of recombinant bacmids 1-12 from C. Background activity in equivalent lysates from uninfected (cells) and unmodified bacmid (AcMNPV) infected cells were more than 106 fold lower.

The bipartite selection resulted in a 20 fold increase in the number of positive colonies compared to the chloramphenicol only selection when the DNA fragment recombining was generated by PCR and a 30 fold increase when released by restriction enzyme digestion of plasmid DNA (FIG. 1B). These differences were significant (t-test, $p=0.03$). For the chloramphenicol selection there was no difference between the number of colonies recovered by PCR and restriction enzyme generated DNA. However, for the bipartite selection the mean number of colonies was four times higher for restriction enzyme released DNA compared to PCR amplified DNA (t-test, $p=0.05$). To confirm that recombinants from the new bipartite selection were genuine, representing modified bacmid containing the inserted expression construct, PCR was carried out on bacmid DNA purified from positive colonies. One primer was designed to a sequence inside the Zeocin resistance marker and one primer targeted a sequence present only in the bacmid DNA flanking the correct insertion site and not in the transfer DNA. Thus PCR product would only be produced where recombination had occurred between the linear DNA used for recombination and the bacmid. 12 separate bacmid DNA samples were tested using this method (FIG. 1C, lanes 1-12), all were positive for the PCR product diagnostic for correctly targeted recombination. In contrast, neither bacmid DNA alone, nor plasmid DNA containing the DNA fragment used for recombination was able to act as template to produce the PCR product (FIG. 1C, lanes 14 and 15, respectively). To further confirm that the recombination had resulted in the recovery of infectious recombinant baculovirus the same 12 PCR positive bacmid clones were transfected into Sf21 cells and passaged twice, then *Renilla* luciferase activity in cells infected with each of the recombinants was assayed at 48 hours post infection. Cells infected with each of the 12 recombinant viruses had *Renilla* luciferase activities that were 106 fold above background (FIG. 1D). Based on these data the inventors proceeded to use the bipartite selection for further investigations.

Example 2

Figure 2A:
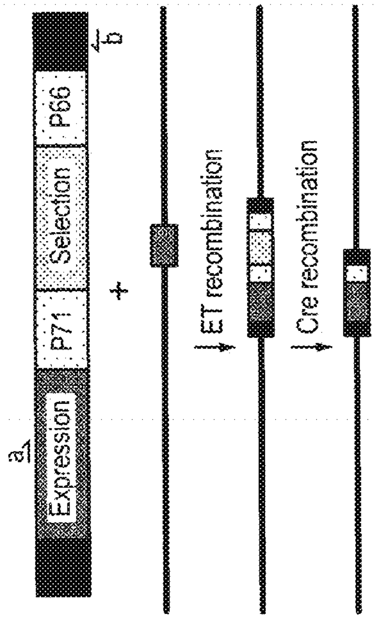
FIG. 2A shows the selective removal of marker genes. Cartoon showing strategy for ET recombination of an expression cassette (expression) into the AcMNPV Bacmid DNA and selective removal of only the marker genes (selection) by Cre mediated recombination.
Figure 2B:
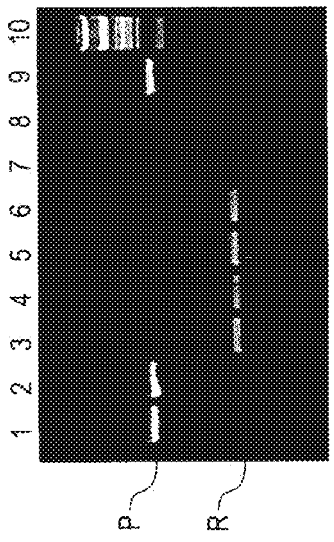
FIG. 2B shows the selective removal of marker genes. PCR using primers labeled a and b in A, lanes 1-2: two independent bacmid recombinants following ET recombination, lanes 3-6: four independent recombinants following Cre mediated recombination to remove the bacterial selectable markers, lane 7: no template, lane 8: unmodified bacmid DNA template, lane 9: plasmid DNA template containing the selectable marker cassette, lane 10: DNA marker. PCR products corresponding to the sizes predicted for the parental and recombinant products of the Cre mediated recombination are labeled P and R respectively.
Figure 2C:
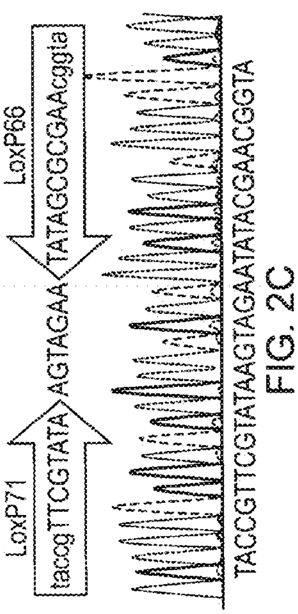
FIG. 2C shows a sequencing trace file of a representative recombinant from the PCR analysis in B confirming the presence of a defective loxP incorporating the loxP71 and loxP66 arms that render the recombinant incapable of undergoing further Cre-mediated recombination (sequences shown in SEQ ID NOS: 1 and 2).
Figure 2D:
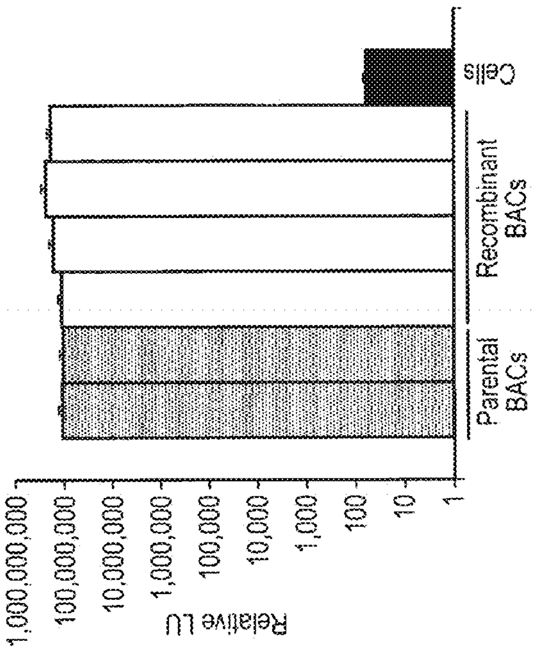
FIG. 2D is a bar graph showing *renilla* luciferase activity of the parental and recombinant bacmids from B when transfected into insect cells. *Renilla* luciferase activity was assayed at 48 hours post infection after passage of the recombinant virus. Background activity from uninfected cells is labeled Cells.

Cre Mediated Removal of the Selectable Marker Allows Multiple Rounds of Recombination with the Same Bipartite Selection In order to express protein complexes with multiple different subunits using single locus insertions, the bipartite marker system was designed such that the selection cassette was flanked by modified LoxP sites. These sites incorporate both the lox66 and lox71 mutations that limit Cre mediated recombination to a single round (1) and a mutation in the spacer reducing homology to wildtype loxP sites. Thus, incubation of modified bacmid with Cre recombinase results in the removal of the bipartite selectable marker and inactivation of the lox recombination site but leaves behind the baculovirus expression cassette (FIG. 2A). To confirm that this strategy could be used successfully to engineer multiple insertions in the bacmid DNA, Cre recombination was used to remove the bipartite marker from bacmid in which the *Renilla* luciferase reporter had been inserted. Recombination was achieved in *E. coli* using the EL350 cell line (2), which has both an integrated lambda prophage expressing exo, bet, and gam under control of the temperature regulated λPL promoter and Cre recombinase under control of an arabinose inducible promoter. EL350 cells containing three of the bacmids modified to incorporate the *Renilla* luciferase-bipartite selection insert (FIG. 1) were induced with arabinose then spread on plates containing kanamycin, to select for the bacmid, and X-gal, to screen for colonies that had lost the selectable marker by Cre mediated recombination. Bacmid DNA was purified from four putative recombinants and Cre mediated recombination confirmed by PCR using primers flanking the selectable markers (FIG. 2B). All four recombinants had PCR products consistent with the size expected from successful Cre recombination. This was further confirmed by sequencing across the modified loxP site of the 4 recombinants (FIG. 2C). The recombinants contained a disabled loxP site that incorporates both the loxP71 and loxP66 mutations and is not competent for further rounds of recombination. To further confirm that Cre mediated bacmid recombinants remained viable in insect cells, bacmid DNA was transfected into insect cells and luciferase activity assayed after two passages as before. All recombinants had *Renilla* luciferase activity that was equivalent to the parental bacmids before Cre recombination (FIG. 2D).

Example 3

Identification of Genetic Loci in the Baculovirus Genome Suitable for High Level Expression of Heterologous Proteins Despite the extensive protein expression work that has been undertaken in the baculovirus expression system most expression has focused on replacement of the polyhedrin or p10 genes to express recombinant proteins. Relatively little literature describes the use of alternative loci for the expression of recombinant protein. In order to test whether selection could be used efficiently at different baculovirus genetic loci, a second round of recombination was carried out on one of the bacmids already containing the *Renilla* luciferase gene. In these experiments, the same polyhedrin promoter-Firefly luciferase-polyhdrin terminator was inserted independently at a total of 13 different genetic loci (ctx, orf11, egt, orf23, v-fgf, 39k, orf51, gp37, iap2, chiA, pe, odv-e18 and odv-e56) generating dual expression baculoviruses for *Renilla* and firefly luciferase proteins (FIG. 3A). Loci were selected as sites for insertion in these experiments by determining which baculovirus genes are non-essential for virus growth in tissue culture, and whether the arrangement of baculovirus genes at particular loci favoured insertion of an additional expression cassette. Nevertheless, some additional changes were made at some loci, particularly changes that resulted in knock-out of particular baculovirus genes (FIG. 3B). Recombinant viruses were passaged twice in Sf21 insect cells and on the third passage cells were harvested at 48 hours post infection, lysed, and assayed for both firefly and *Renilla* luciferase activities. *Renilla* luciferase activity was used as a marker for virus replication and protein expression as all the recombinants had the same p35 promoter driven *Renilla* luciferase cassette in the p10 locus. Expression of firefly luciferase at each new locus was compared to a virus carrying firefly luciferase gene at the polyhedrin locus and the same *Renilla* luciferase reference gene. Of the 13 loci tested, 9 had *Renilla* luciferase activities which were at least $10^5$ fold above background and of these 8 (ctx, egt, orf51, gp37, iap2, chiA, odv-e18 and odv-e56) had *Renilla* luciferase activity which was at or above the activity measured for the parental *Renilla* luciferase only, and polyhedrin locus firefly luciferase controls (FIG. 3C). The four loci (orf11, v-fgf, pe and orf23) which resulted in virus which gave *Renilla* luciferase activity that was within 10 fold of the background activity were excluded from further analysis. For the remaining viruses, the *Renilla* luciferase activity was used as a reference to normalise firefly luciferase activity and obtain a measure of relative expression of the firefly luciferase from each locus (FIG. 3D). 7 loci (ctx, egt, 39k, orf51, gp37, iap2 and odv-e56) had firefly luciferase activity which was at least $10^6$ fold higher than background and similar to that when the same gene was expressed from the polyhedrin locus (FIG. 3D). Two viruses (chiA and odv-e18) had high levels of *Renilla* luciferase but relatively poor expression of firefly luciferase.

This study reveals that high level expression of foreign proteins is possible from several genetic loci within the baculovirus genome and identifies seven loci (ctx, egt, 39k, orf51, gp37, iap2 and odv-e56), in addition to polyhedrin and p10 that give good expression. Of these sites 39k, orf51 and gp37 are insertions into the DNA flanking the coding region of the gene and do not directly interrupt protein expression. In contrast, insertions into the ctx, egt, iap2 and odv-e56 each would be expected to prevent expression of the corresponding proteins from these genes. The first three of these genes have previously been described as non-essential to the growth of the virus in cell culture (3-6). Truncation of the ODV-E56 protein has also been reported (7).

Of the loci that did not give good expression of the firefly luciferase reporter, four (orf11, v-fgf, pe and orf23) also resulted in a reduced expression of *Renilla* luciferase marker protein which was present in all recombinants. As the focus of the study was to identify sites which were suitable for insertion of very late promoter expression constructs the precise reason for this reduced expression was not investigated. Possibilities include locus-specific effects on virus replication or transcription, and disruption of essential promoter or enhancer elements for flanking genes. The low level expression of firefly luciferase in the chiA and odv-e18 insertion viruses was unexpected for different reasons. Other reports have recorded insertion of recombinant protein expression cassettes into the chiA locus (8, 9). It is possible that the reduced level of expression seen with the firefly luciferase gene in this locus in our experiments is due to the effects on genes flanking the insertion. For odv-e18, recent reports using the same mutant virus have suggested that this protein is essential for budded virus production and cell to cell movement (10, 11). These studies were based on mutants in which there was a deletion within the coding sequence of odv-e18 and the upstream flanking gene. In the experiments, where odv-e18 was inactivated by mutation of the ATG of the coding sequence to GAT followed by insertion of the firefly luciferase cassette at this point in the gene it was possible to recover infectious virus. Expression of *Renilla* luciferase on the third passage equivalent to that in the parental virus suggests that there was no impairment of the ability of this mutant virus to replicate. However, given the ~2 log reduction in firefly luciferase levels compared to virus without this mutation it is not possible to rule out the possibility that a small population of virus in which the mutation was repaired was complementing a second population expressing the reporter gene.

Example 4

Expression of Protein Complexes Using Multi-Locus Baculovirus Expression

Example 3 focused on the use of reporter genes to quantitatively assess the potential of different baculovirus loci to express recombinant protein. To establish whether it is possible to express and recover recombinant protein complexes, three specific complexes were targeted with different numbers of protein subunits. Virus-like particles were produced for Influenza (A/seal/Mass/1/80) H7 subtype by co-expression of the viral M1 and HA proteins (2 protein complex), and for Bluetongue virus (BTV) serotype 1 by co-expression of VP2, VP3, VP5 and VP7 (4 protein complex). In addition, the inventors targeted expression of all 8 subunits of the mouse CCT chaperone complex to be used for further functional and structural studies.

Influenza A VLPs

For these experiments all influenza genes were from the SC35M mouse adapted strain derived from the H7N7 (A/seal/Mass/1/80) isolate, obtained from researchers at Philipps University Marburg, Germany To test whether the multi-locus expression system was able to produce protein complexes with two proteins, the coding sequence for the influenza A M1 protein was initially inserted into the egt locus under the control of the polyhedrin promoter. For comparison, the same gene was inserted into a conventional baculovirus expression vector (pAc-YM1) targeting the polyhedrin locus. Following recombination, both resulting baculoviruses expressed the M1 protein. Levels of expression of the protein from the egt and polyhedrin loci were both significantly higher than for any other viral or cellular protein in baculovirus infected cells when assessed by coomassie stained SDS-PAGE (FIG. 4).

Figure 5A:
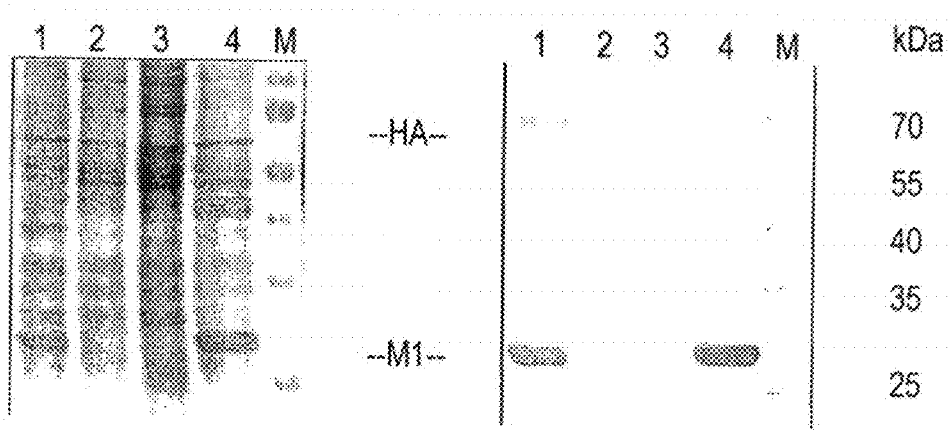
FIG. 5A shows co-expression of influenza M1 and HA and formation of VLPs. Left panel shows Coomassie stained gel of total protein; right panel shows western blot of duplicate gel probed with anti-H7N7 influenza virus serum. Cells were infected with dual baculovirus expressing HA and M1 (lane 1), baculovirus expressing HA only (lane 2), cells control (lane 3), baculovirus expressing M1 only (lane 4).
Figure 5B:
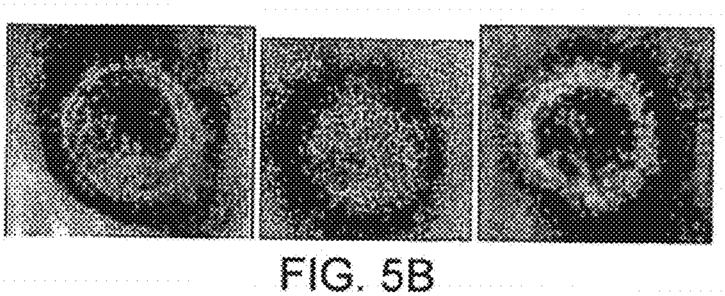
FIG. 5B shows negative stain EM images of influenza VLPs.
Figure 5C:
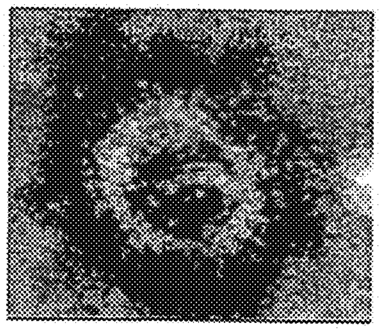
FIG. 5C shows negative stain EM images of immunogold (HA) labelled influenza VLPs with gold particles arrowed.

To generate a dual virus expressing both M1 and HA, the bacterial selection cassette was removed from the M1 expressing Bacmid by Cre recombination and the HA gene from the same influenza strain (A/seal/Mass/1/80) inserted at the p10 locus by a second round of ET recombination. Co-expression of M1 and HA from the resulting virus were confirmed by SDS-PAGE and western blot analysis as before (FIG. 5A). In addition, influenza VLPs were isolated from the culture medium of infected cells, purified by density gradient ultracentrifugation and visualised by negative stain EM analysis (FIG. 5B). To ensure that VLPs visualised were indeed influenza, particles were immunogold labeled using antibodies specific for influenza HA (FIG. 5C).

Taken together, these data were good evidence that the multilocus approach could be used successfully for recombinant protein expression and that it was practical to produce such a recombinant virus through two rounds of insertion of the bipartite selectable marker system. Flu VLP have been widely tested by others and shown to be immunogenic in mice and ferrets. This method of constructing the VLP has the advantage that it is possible to have the baculovirus genome with M1 already pre-integrated and ready for expression. Thus, to make VLP it should only be necessary to perform a single round of recombination to add the HA gene from whatever emerging flu subtype is required for vaccine production. For VLP based flu vaccines this would simplify the necessary cloning and potentially increase the speed with which new types of VLP could be made.

BTV1 VLPs

Unlike influenza, where VLP can be formed by expression of just two proteins, BTV VLP require the co-ordinated expression of four structural proteins (VP2, VP3, VP5 and VP7). In order to further demonstrate the usefulness of the new system for recombination, viruses were produced that expressed each protein singly and the combination of all four BTV structural proteins (FIG. 6). One of the advantages of the new system is that viruses expressing single proteins and multiple proteins can be made from the same set of transfer vectors. This facilitates production of control viruses expressing single proteins to act as markers for the position of proteins co-expressed in the full complex. For the BTV VLP a different set of loci were used from those in the influenza example (FIG. 6C). In addition, the new system was combined with the orf1629 knockout Bacmid described by Zhao et al., (12) to allow use of a conventional transfer vector at the polyhedrin locus to express one of the subunits of the complex. Formation of VLPs was confirmed by particle morphology under negative stain EM, combined with immunogold labelling for one of the outer capsid proteins (VP5) (FIG. 6D).

Mouse CCT

Figure 7:
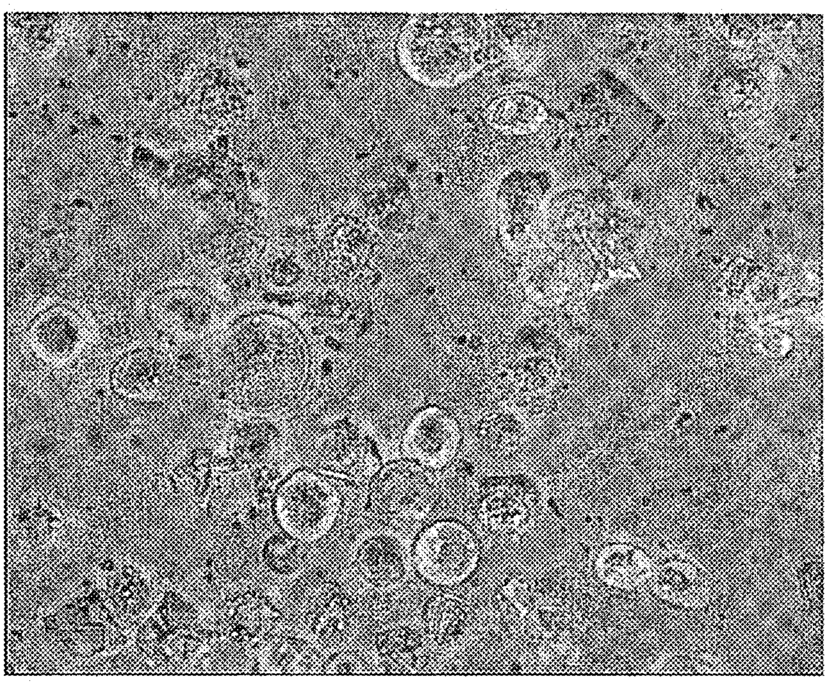
FIG. 7 shows crystalline plates formed on overexpression of CCT5. Quadrilateral protein aggregates in culture media of very late infections with baculovirus expressing CCT5.

The application of the present invention is not limited to the formation of virus-like particles. Indeed, as many cellular proteins are present in cells as complexes with more than one subunit, the efficient formation of these complexes has application to a range of fields. To demonstrate the usefulness of the system to other studies the chaperone complex CCT was chosen. This complex has implications in cancer research and with 8 subunits represents a significant challenge for protein expression. Indeed it would not have been possible to express this complex in the baculovirus system without the vectors and methods of the present invention. Eight transfer vectors, each expressing one of the subunits for the mouse CCT and each targeting a different locus, identified in Example 3 above, were constructed. These were used to generate recombinant virus expressing each subunit alone and combinations of subunits. For one of the subunits (CCT5) an unusual phenotype was noted when the protein was over expressed in cells. Crystalline needles were noted inside cells and, late in infection when cells had ruptured, quadrilateral plates of crystalline material were noted in the culture medium (FIG. 7). A purification scheme was generated for this protein and this was supplied with preliminary crystallisation conditions and infected cell material to the collaborator for the CCT part of the project.

Although expression of some of the other CCT subunits resulted in visible aggregates in cells late in infection, none resulted in aggregates with such a regular appearance.

All 8 CCT subunits had high level expression (FIG. 8A) and cross reacted with a polyclonal antiserum raised to mouse CCT. There was some cross reaction between one of the endogenous insect cell CCT subunits and the polyclonal antibody (FIG. 8B, lane 9). However, this endogenous signal only co-located with 3 subunits (CCT1, CCT5 and CCT6) which all accumulated to high level in infected cells and thus were clearly detectable. All other subunits migrated as slightly different molecular mass proteins and thus could be distinguished from the insect cell protein on the basis of migration.

CONCLUSIONS

For all three protein complexes there were clear differences in the accumulation of the same recombinant protein when expressed alone or in presence of other proteins. In almost all cases there was a reduction in the level of protein expression when multiple proteins were expressed from the same virus. This was to a certain extent expected. Competition for proteins required for transcription, RNA processing, translation and protein folding would predict that two highly expressed baculovirus genes would have lower expression together than separately. However what was striking for both the BTV VLP and CCT examples was that reduction in protein expression was variable between different genetic loci. For example with BTV, VP2, VP5, VP3 and VP7 all resulted in significant and similar accumulation of protein when expressed on their own. However, when combined in a single baculovirus expressing all four proteins, VP2 and VP3 accumulated to lower levels than VP5 and VP7 (FIG. 6A). This effect cannot be explained by the position effect of genomic integration since in both the single and quadruple viruses the genes were expressed from the same genetic loci. One possible explanation would be that the effect was due to the different promoters that were used for the different genes. Both VP5 and VP7 were expressed under control of the p10 promoter and VP2 and VP3 were under control of the polyhedrin promoter. This would be consistent with a report in the literature where deletion of the p10 gene resulted in increased expression from polyhedrin locus 13. Thus duplication of the polyhedrin promoter in the presence of two p10 promoters would be predicted to selectively reduce expression from the polyhedrin promoter driven genes. However, this cannot be a complete explanation for the effect observed in the case of the CCT complex. Both CCT5 and CCT2 were expressed from the p10 promoter and gave high steady-state levels of recombinant protein when expressed alone (FIGS. 8A and B, lanes 2 and 5). However, when combined in the same virus, expression of CCT5 was substantially reduced compared to CCT2 (FIGS. 8A and B, lane 10). From these data, other cis acting sequences present at the p10 locus may be contributing to the enhanced relative expression of CCT2 and BTV VP5, which were both inserted at this locus. The relatively low apparent expression of influenza HA when inserted at the same site may be more related to turnover of this protein in the ER rather than transcriptional effects. Both CCT2 and VP5 accumulate in the cytoplasm.

The inventors have improved the efficiency of the ET recombination system as applied to baculovirus to the point that it can be used for routine insertion of expression cassettes for recombinant proteins. Furthermore, they have identified seven genetic loci (ctx, egt, 39k, orf51, gp37, iap2 and odv-e56) that can be used for high level expression of protein and demonstrated that multi-protein complexes can be assembled using this system using three examples (influenza A and BTV VLPs, and CCT complex).

All documents cited above are incorporated herein by reference.

REFERENCES CITED

1. Albert, H., Dale, E. C., Lee, E. & Ow, D. W. Plant J 7, 649-59. (1995).
2. Lee, E. C. et al. Genomics 73, 56-65 (2001).
3. Eldridge, R., Li, Y. & Miller, L. K. J Virol 66, 6563-71 (1992).
4. Flipsen, J. T., Mans, R. M., Kleefsman, A. W., Knebel-Morsdorf, D. & Vlak, J. M. J Virol 69, 4529-32 (1995).
5. O'Reilly, D. R. & Miller, L. K. Science 245, 1110-2 (1989).
6. Griffiths, C. M. et al. J Gen Virol 80 (Pt 4), 1055-66 (1999).
7. Braunagel, S. C., Elton, D. M., Ma, H. & Summers, M. D. Virology 217, 97-110 (1996).
8. Berger, I., Fitzgerald, D. J. & Richmond, T. J. Nat Biotechnol 22, 1583-7 (2004).
9. Fitzgerald, D. J. et al. Nat Methods 3, 1021-32 (2006).
10. McCarthy, C. B., Dai, X., Donly, C. & Theilmann, D. A. Virology 372, 325-39 (2008).
11. McCarthy, C. B. & Theilmann, D. A. Virology 375, 277-91 (2008).
12. Zhao, Y., Chapman, D. A. & Jones, I. M. Nucleic Acids Res 31, E6-6. (2003).
13. Chaabihi, H. et al. J Virol 67, 2664-71 (1993).
14. Summers, M. D. Adv Virus Res 68, 3-73 (2006).
15. Emery, V. C. & Bishop, D. H. Protein Eng 1, 359-66 (1987).
16. French, T. J., Marshall, J. J. & Roy, P. J Virol 64, 5695-700 (1990).
17. Latham, T. & Galarza, J. M. J Virol 75, 6154-65. (2001).
18. Pushko, P. et al. Vaccine 19, 142-53. (2000).
19. Ye, L. et al. Virology 351, 260-70 (2006).
20. Berger, I., Fitzgerald, D. J. & Richmond, T. J. Nat Biotechnol 22, 1583-7 (2004).
21. Fitzgerald, D. J. et al. Nat Methods 3, 1021-32 (2006).
22. French, T. J. & Roy, P. J Virol 64, 1530-6 (1990).
23. Devos, D. & Russell, R. B. Curr Opin Struct Biol 17, 370-7 (2007).
24. O'Neal, C. M., Clements, J. D., Estes, M. K. & Conner, M. E. J Virol 72, 3390-3 (1998).
25. Palomares, L. A., Lopez, S. & Ramirez, O. T. Biotechnol Bioeng 78, 635-44. (2002).
26. Mena, J. A., Ramirez, O. T. & Palomares, L. A. BMC Biotechnol 7, 39 (2007).
27. Weyer, U. & Possee, R. D. J Gen Virol 72 (Pt 12), 2967-74 (1991).
28. Bertolotti-Ciarlet, A., Ciarlet, M., Crawford, S. E., Conner, M. E. & Estes, M. K. Vaccine 21, 3885-900 (2003).
29. Kamita, S. G., Maeda, S. & Hammock, B. D. J Virol 77, 13053-61 (2003).
30. Crouch, E. A. & Passarelli, A. L. J Virol 76, 9323-34 (2002).
31. Mikhailov, V. S., Okano, K. & Rohrmann, G. F. J Virol 77, 2436-44 (2003).
32. Pijlman, G. P. et al. J Virol 76, 5605-11 (2002).
33. Pijlman, G. P., van den Born, E., Martens, D. E. & Vlak, J. M. Virology 283, 132-8 (2001).
34. Pijlman, G. P., van Schijndel, J. E. & Vlak, J. M. J Gen Virol 84, 2669-78 (2003).
35. Vanarsdall, A. L., Pearson, M. N. & Rohrmann, G. F. Virology 367, 187-95 (2007).
36. Vanarsdall, A. L., Mikhailov, V. S. & Rohrmann, G. F. Virology 364, 475-85 (2007).
37. Okano, K., Vanarsdall, A. L. & Rohrmann, G. F. Virology 359, 46-54 (2007).
38. Vanarsdall, A. L., Okano, K. & Rohrmann, G. F. J Virol 80, 1724-33 (2006).
39. Okano, K., Vanarsdall, A. L. & Rohrmann, G. F. J Virol 78, 10650-6 (2004).
40. Vanarsdall, A. L., Okano, K. & Rohrmann, G. F. Virology 326, 191-201 (2004).
41. Fang, M., Dai, X. & Theilmann, D. A. J Virol 81, 9859-69 (2007).
42. Wang, Y. et al. Virology 367, 71-81 (2007).
43. Yamagishi, J., Burnett, E. D., Harwood, S. H. & Blissard, G. W. Virology 365, 34-47 (2007).
44. Xi, Q., Wang, J., Deng, R. & Wang, X. Virus Genes 34, 223-32 (2007).
45. Li, Y. et al. Virus Genes 31, 275-84 (2005).
46. Stewart, T. M., Huijskens, I., Willis, L. G. & Theilmann, D. A. J Virol 79, 4619-29 (2005).
47. Kamita, S. G. et al. Proc Natl Acad Sci USA 102, 2584-9 (2005).
48. Milks, M. L., Washburn, J. O., Willis, L. G., Volkman, L. E. & Theilmann, D. A. Virology 310, 224-34 (2003).
49. Zhao, Y., Chapman, D. A. & Jones, I. M. Nucleic Acids Res 31, E6-6 (2003).

The invention claimed is:

1. A suite of transfer vectors for inserting a plurality of genes that encode a plurality of proteins that are subunits of a protein complex into a baculovirus sequence comprising:

i) a plurality of transfer vectors, wherein each transfer vector comprises an expression cassette comprising a eukaryotic promoter operably linked to at least one of the said genes; and ii) sequences flanking both sides of the expression cassette, wherein the sequences substantially correspond to sequences within a selected one of the genetic locus within the baculovirus selected from: ctx, egt, 39k, orf51, gp37, iap2 and odv-e56 and wherein different transfer vectors have different said flanking sequences.

2. A method for producing a recombinant bacmid, comprising:

bringing a bacmid and the suite of transfer vectors of claim 1 together to allow homologous recombination; and selecting for a recombinant bacmid that comprises an expression cassette.

3. A method for producing a recombinant baculovirus comprising producing a recombinant bacmid by the method of claim 2 and culturing a eukaryotic cell containing the bacmid so that a baculovirus is produced.

4. The suite of transfer vectors of claim 1, wherein the plurality of transfer vectors are bacmids.

5. The suite of transfer vectors of claim 1, wherein the plurality of proteins interact to form a protein complex.

6. The suite of transfer vectors according to claim 5, wherein the protein complex is a virus like particle, or a chaperone complex.

7. The suite of transfer vectors of claim 1, wherein the plurality of transfer vectors comprise a recombinant baculovirus.

8. A cell in culture containing the suite of transfer vectors of claim 1.

9. A method for producing one or more proteins comprising culturing the suite of transfer vectors of claim 1.

* * * * *

SEQUENCE LISTING

```
<160> NUMBER OF SEQ ID NOS: 1

<210> SEQ ID NO 1
<211> LENGTH: 33
<212> TYPE: DNA
<213> ORGANISM: artificial
<220> FEATURE:
<223> OTHER INFORMATION: defective LoxP site

<400> SEQUENCE: 1

taccgttcgt ataagtagaa tatacgaacg gta                              33
```